(12) United States Patent
McKenzie et al.

(10) Patent No.: US 8,632,549 B2
(45) Date of Patent: Jan. 21, 2014

(54) SURGICAL TOOL FOR PECTUS BAR EXTRACTION

(75) Inventors: Frederic McKenzie, Virginia Beach, VA (US); Sebastian Bawab, Chesapeake, VA (US); Krzysztof Rechowicz, Norfolk, VA (US); Robert Obermeyer, Norfolk, VA (US)

(73) Assignees: Old Dominion Resarch Roundation, Norfolk, VA (US); Children's Surgical Specialty Group, Inc., Norfolk, VA (US)

( * ) Notice: Subject to any disclaimer, the term of this patent is extended or adjusted under 35 U.S.C. 154(b) by 352 days.

(21) Appl. No.: 12/692,232

(22) Filed: Jan. 22, 2010

(65) Prior Publication Data

US 2011/0184411 A1    Jul. 28, 2011

(51) Int. Cl.
*A61B 17/58* (2006.01)
*A61B 17/60* (2006.01)
*A61F 2/00* (2006.01)
*B25C 11/00* (2006.01)
*B66F 15/00* (2006.01)

(52) U.S. Cl.
USPC .......... 606/99; 254/21; 254/25; 254/28; 254/19

(58) Field of Classification Search
USPC ....... 606/86 A, 86 B, 86 R, 99, 100; 81/53.2; 7/166; 254/21, 25, 28, 19; 29/278, 270
See application file for complete search history.

(56) References Cited

U.S. PATENT DOCUMENTS 5,702,463 A * 12/1997 Pothier et al. .............. 623/20.32
7,621,916 B2 * 11/2009 Lauryssen et al. .......... 606/86 R

* cited by examiner

*Primary Examiner* — Andrew Yang
*Assistant Examiner* — Diana S Jones
(74) *Attorney, Agent, or Firm* — Novak Druce Connolly Bove + Quigg LLP

(57) ABSTRACT

A pectus bar extraction tool for removing a pectus bar having posterior and anterior sides includes a handle, an engagement member fixed to and extending from the handle for extending from the anterior to the posterior sides of the pectus bar to engage the posterior side of the pectus bar, and a lever arm fixed to and extending from the handle opposite to the engagement member for engaging the pectus bar on the anterior side of the pectus bar. A system and method for removing a pectus bar are also disclosed.

7 Claims, 6 Drawing Sheets

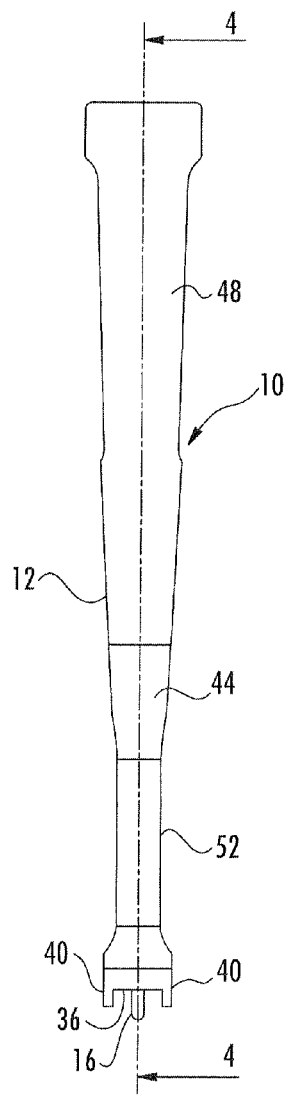
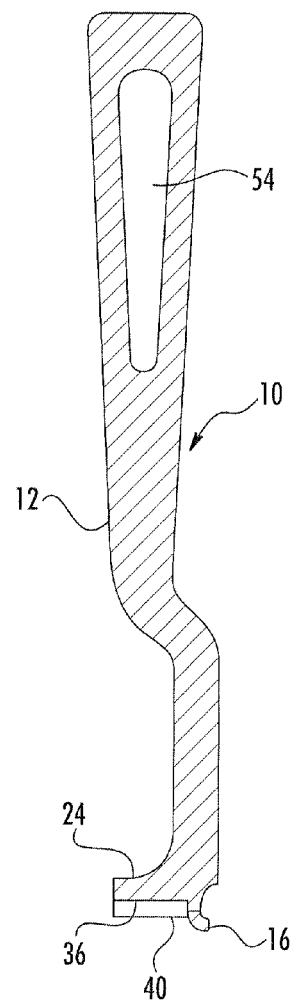
FIG. 3
FIG. 4

SURGICAL TOOL FOR PECTUS BAR EXTRACTION

BACKGROUND OF THE INVENTION

Pectus excavatum (PE), also called sunken or funnel chest, is a congenital chest wall deformity which is characterized, in most cases, by a deep depression of the sternum. Very often other problems can accompany this condition, like scoliosis and breathing issues. The correction of pectus excavatum (PE) and similar chest deformities has two main goals. Using the minimally-invasive Nuss procedure, one or two metal bars are placed to change the chest geometry which, in most cases, effects a positive result on a patient's physiology. Secondly, subjective aesthetic improvement may be achieved.

According to the Nuss procedure, incisions are made under the skin in the lateral chest wall at each lateral side of the patient and a skin tunnel is raised from the incision to the top of the pectus ridge. A tool known as a pectus introducer is inserted through the incision and used to create a tunnel for the pectus bar. The pectus introducer is advanced under the sternum and then through the opposite lateral incision. The pectus bar is shaped to fit the patient. The pectus bar is then inserted through the tunnel, with the convexity facing posteriorly. The pectus bar is then inverted to raise the sternum and anterior chest wall. The pectus bar is secured in place, for which one or more stabilizers can be used, and the incisions are closed.

The pectus bar remains in the patient for a treatment period lasting about 2 years or until the physician determines that the correction is complete and then is removed. Tissue grows around and in some cases directly adheres to the pectus bar, making removal difficult. Currently, surgical tools for removing the bars have proved inadequate for many surgeons.

SUMMARY OF THE INVENTION

A pectus bar extraction tool for removing a pectus bar having posterior and anterior sides, includes a handle, an engagement member and a lever arm. The engagement member is fixed to and extends from the handle extending from the anterior to the posterior side of the pectus bar to engage the posterior side of the pectus bar. The lever arm is fixed to and extends from the handle opposite to the engagement member to rest upon the pectus bar on the anterior side of the pectus bar and act as a fulcrum.

The engagement member can provide a protrusion adapted for placement through an aperture in the pectus bar. The protrusion can be a hook. The width of the hook can be less than one-half of the width of the pectus bar. The hook extends distally to the handle.

The lever arm can comprise lateral side members for engaging lateral side portions of the pectus bar. A web can be provided between the lateral side members, and can be dimensioned so that the pectus bar will fit between the lateral side members and contact the web. The lateral side members can be rails.

The handle can include an indented portion. The indented portion assists in gripping when the handle is in proximity to a surface, such as an operating room table.

A system for correcting pectus excavatum can include a pectus bar and a pectus bar extraction tool. The pectus bar has an elongated main body portion with posterior and anterior sides and opposing ends, and structure at the ends for engaging the pectus bar extraction tool. The pectus bar extraction tool can include a handle and an engagement member fixed to the handle for cooperating with the engagement structure on the pectus bar to engage the extraction tool to the pectus bar. The engagement member of the pectus bar extraction tool can extend under the pectus bar to engage the posterior side of the pectus bar. The pectus bar extraction tool can have a lever portion for engaging the pectus bar on the anterior side.

A method for extracting a pectus bar from a patient includes the step of providing a pectus bar having an elongated main body portion with posterior and anterior sides and opposing ends, and engagement structure at the ends for engaging a pectus bar extraction tool, the pectus bar having been surgically implanted in the patient. A pectus bar extraction tool having a handle and an engagement member fixed to the handle for cooperating with the engagement structure on the pectus bar is also provided. The engagement member on the pectus bar extraction tool is engaged to the engagement structure on an opposing end of the pectus bar. A second pectus bar extraction tool can be engaged to the engagement structure at the other opposing end of the pectus bar. Using the handles, the extraction tools are manipulated to apply a straightening force to the pectus bar so as to at least partially straighten the pectus bar, whereby the pectus bar can be removed from the patient.

BRIEF DESCRIPTION OF THE DRAWINGS

There is shown in the drawings embodiments which are presently preferred, it being understood, however, that the invention can be embodied in other forms without departing from the spirit or essential attributes thereof.

FIG. 3 is a front elevation.

FIG. 4 is a cross section taken along line 4-4 in FIG. 3.

DETAILED DESCRIPTION OF THE INVENTION

Figure 1:
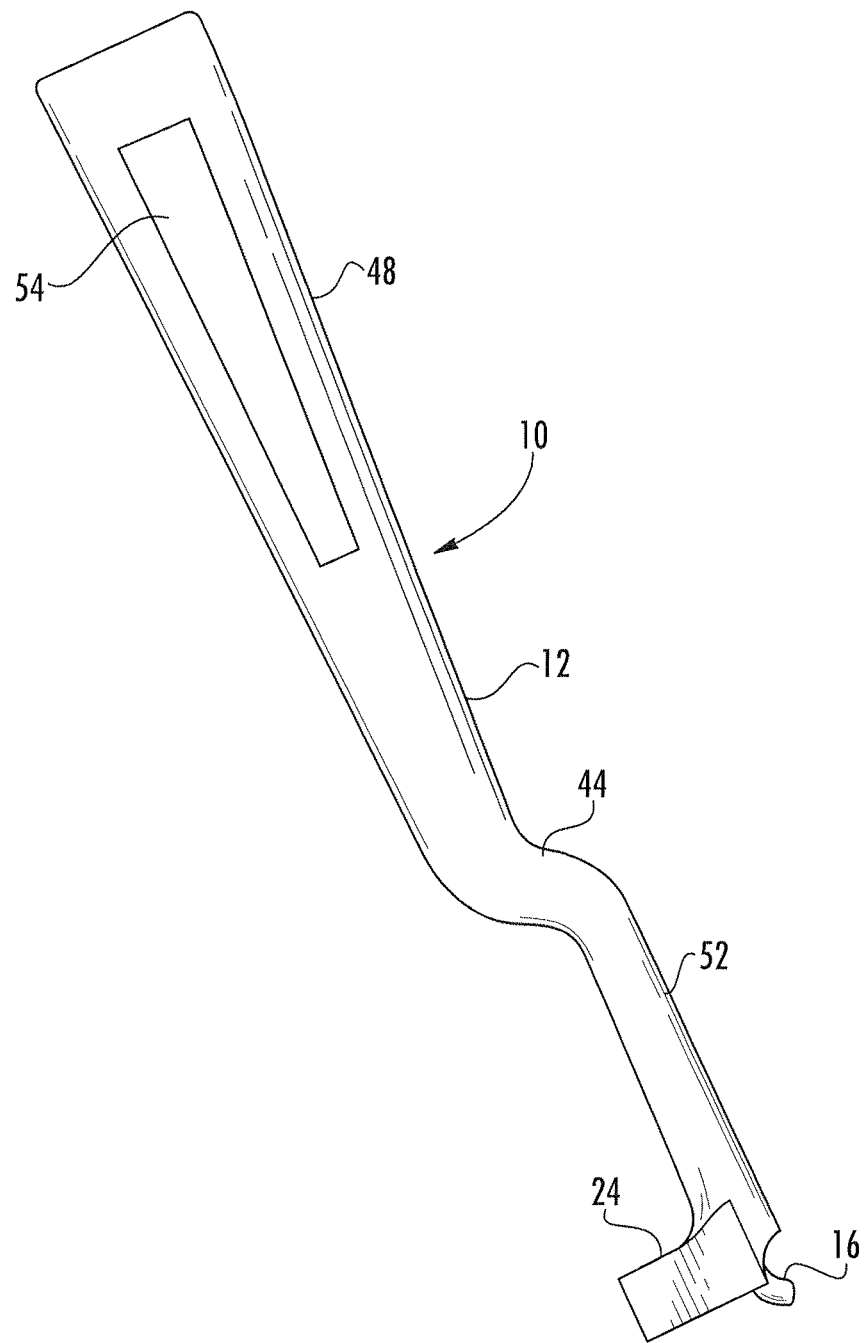
FIG. 1 is a side elevation of a pectus bar extraction tool according to the invention.
Figure 2:
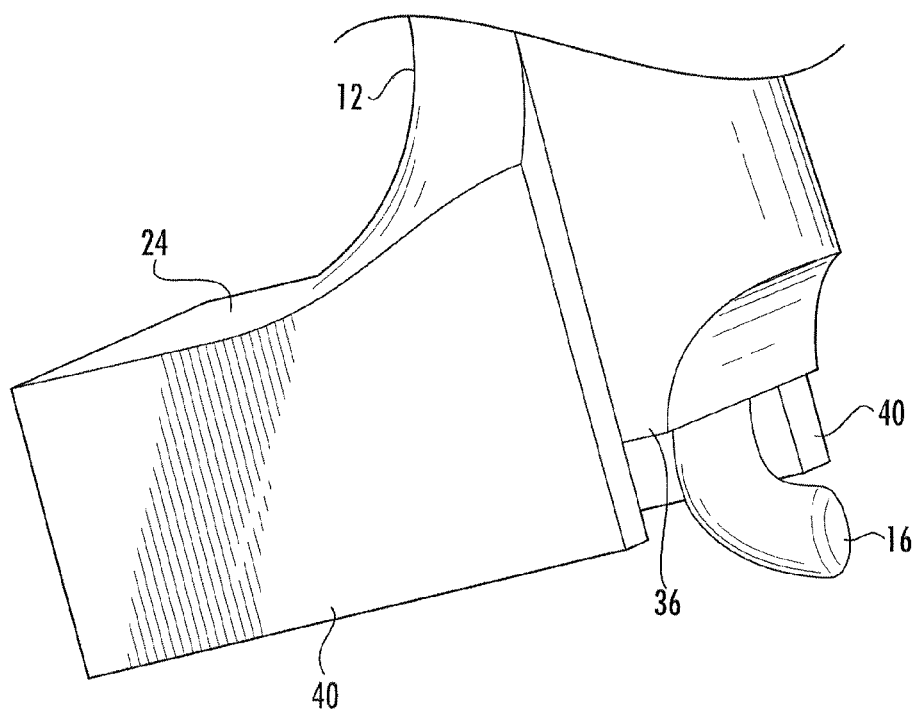
FIG. 2 is a perspective view of a distal end of the extraction tool.

A pectus bar extraction tool according to the invention is shown in FIGS. 1-7. The extraction tool 10 according to the invention includes an elongated handle 12. An engagement member 16 is fixed to and extends from the handle 12. The engagement member 16 extends under a pectus bar 20 to engage the posterior side 32 of a pectus bar 20. A lever arm 24 is fixed to and extends from the handle 12 oppositely from the engagement member 16 for engaging the pectus bar 20 on the anterior side 28 of the pectus bar 20.

The engagement member 16 can be in the shape of a protrusion extending distally and outwardly relative to the handle 12 so as to provide a hook or claw shape. The dimensions of the engagement member can vary, and in one aspect the width of the hook is less than one-half the width of the pectus bar 20. The hook or other engagement member 16 can be provided with a rounded or blunt end so as to avoid damage to tissue during the pectus bar removal process. Other dimensions and configurations of the engagement member 16 are possible. A tongue and groove engagement, a flange and slot, hooks and loops, or various other detachable mechanical engagement structures are possible. The attachment should be secure enough to apply the forces required to straighten the pectus bar 20 and to free the pectus bar from surrounding tissue, and the attachment should be made from the anterior side 28 of the pectus bar 20 to the extent possible so that excessive cutting or tearing of tissue is not required to position the engagement member under or around the pectus bar 20.

Figure 5:
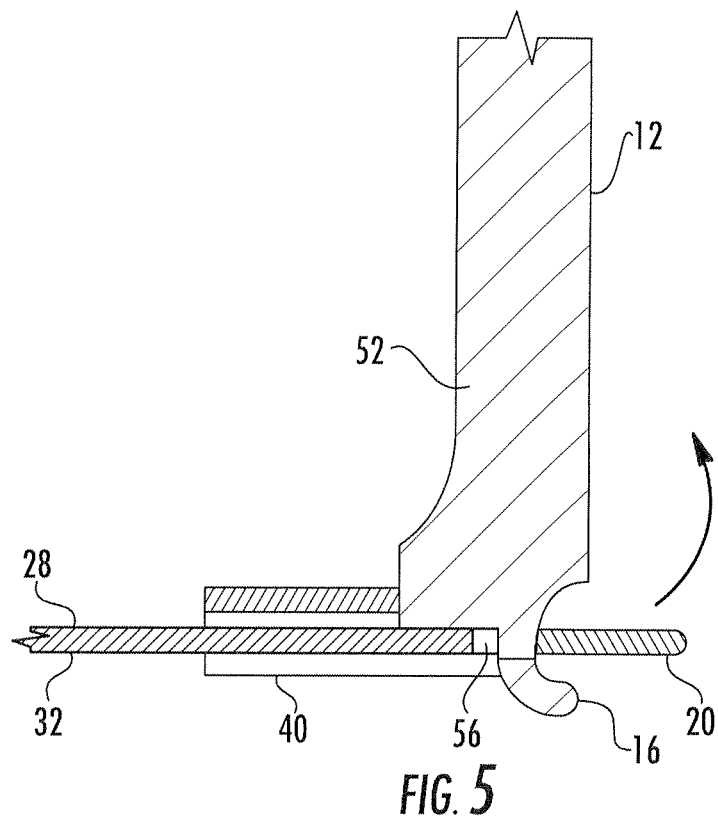
FIG. 5 is a cross section illustrating the extraction tool engaged to a pectus bar.

The lever arm 24 engages an anterior surface 28 of the pectus bar 20 while the engagement member 16 engages a posterior surface 32 (FIG. 5). The handle 12 can then be manipulated to rotate the engagement member 16 in the direction of the arrow, and the lever arm 24 will contact the anterior surface 28 so as to straighten the pectus bar 20 and to pry the pectus bar 20 from tissue to which it may be connected.

The lever arm 24 can comprise a web 36 and lateral side members such as rails 40. The web 36 provides a contact surface for the pectus bar 20 that is a distance from the handle 12 and engagement member 16 so as to act as a lever to lend additional force to the engagement member 16 and pry the pectus bar 20 from surrounding tissue. The lateral side members are positioned so as to receive the pectus bar 20 between them, and with the web 36, to provide for secure engagement of the pectus bar 20 so that the engagement member 16 does not become disengaged from the pectus bar 20 and is stabilized on the bar.

The handle 12 can be fashioned in different shapes and sizes. In one embodiment, the handle 12 has a curved portion 44 to offset the proximal portion 48 of the handle which is gripped by the user, from the distal portion 52. This will allow for gripping of the proximal portion 48 of the handle 12 when it is horizontal and adjacent to a surface such as an operating room table. An opening 54 can be provided in the proximal portion 48 to further facilitate gripping. The length of the handle can be adjusted for the preference of the user, the amount of leverage that is necessary, or the particular removal procedure that will be performed.

The invention can be used with pectus bars having a variety of shapes and sizes. The pectus bar 20 has at least one aperture 56. The engagement member 16 extends through the aperture 56 so as to engage the posterior surface 32. The pectus bar 20 is generally elongated and planar, and with differing dimensions according to the size and shape of the patient and the particular characteristics of the patient. The pectus bar 20 is usually made from a material that is pliable, so that the pectus bar 20 can be shaped in the operating room by the surgeon to fit the particular patient. The pectus bar 20 can be made from surgical quality metals or plastics.

Figure 6:
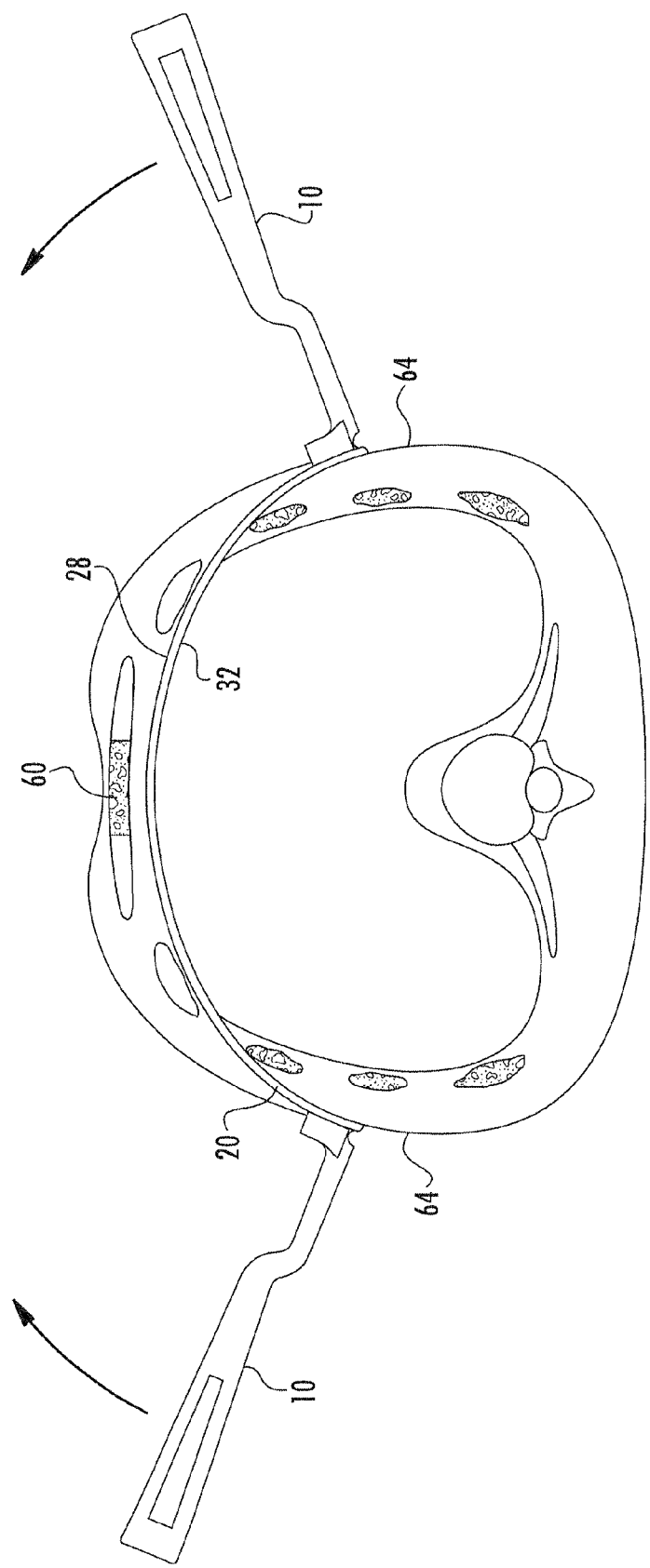
FIG. 6 is a cross section through the human anatomy illustrating the use of extraction tools according to the invention to remove a pectus bar according to a method of the invention, in a first mode of operation.
Figure 7:
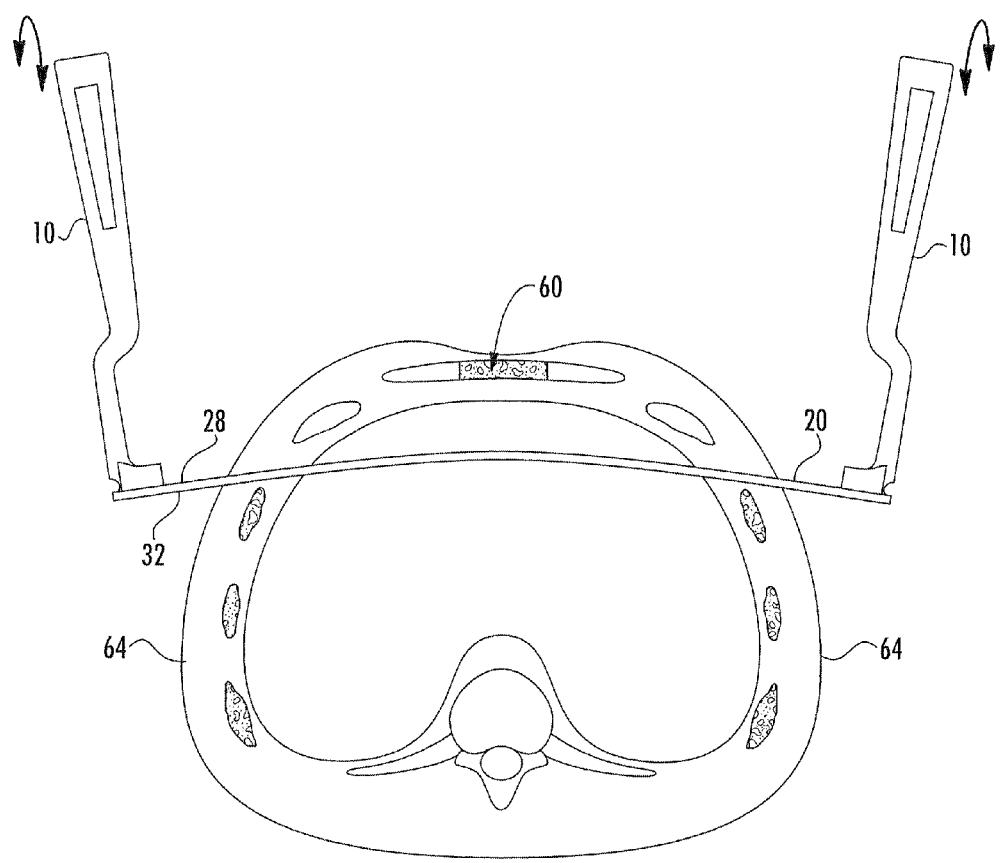
FIG. 7 is a cross section through the human anatomy illustrating the use of extraction tools to remove a pectus bar according to a method of the invention, in a second mode of operation.

A method for extracting a pectus bar from a patient is shown in FIGS. 6-7. The engagement member 16 of the pectus bar extraction tool 10 is positioned through the aperture 56 and thereby engaged to the pectus bar 20. Preferably two extraction tools 10 are provided, one for each end of the pectus bar 20 at each lateral side 64 of the patient. The second pectus bar extraction tool is engaged to the engagement structure at the other end of the pectus bar 20. The handles of the pectus bar extraction tools 10 are used to apply a straightening force to the pectus bar so as to at least partially straighten the pectus bar 20, as depicted by the arrows in FIG. 6. A twisting motion can then be applied to the handles to assist in dislodging the pectus bar 20 from surrounding tissue, as depicted by the arrows in FIG. 7. The pectus bar 20 can then be removed from the patient from a position posterior to the sternum 60.

This invention can be embodied in other forms without departing from the spirit or essential attributes thereof and, accordingly, reference should be had to the following claims rather than the foregoing specification as indicating the scope of the invention.

We claim:

1. A pectus bar extraction tool for removing a pectus bar from a patient, the pectus bar having posterior and anterior sides, comprising a handle having a long axis, an engagement member fixed to and extending distally and laterally outward from the handle for extending from the anterior to the posterior sides of the pectus bar to engage the posterior side of the pectus bar, the engagement member being a protrusion adapted for placement through an aperture in the pectus bar, and a lever arm fixed to and extending laterally from the handle opposite to the engagement member for engaging the pectus bar on the anterior side of the pectus bar, wherein the lever arm comprises spaced-apart lateral side members for engaging lateral side portions of the pectus bar, and a web between the lateral side members, the lateral side portions and the web defining an open-ended channel, the open-ended channel being transverse to the long axis of the handle, the pectus bar fitting between the lateral side members to contact the web and extending from each of the open ends of the channel, the protrusion being centrally located relative to the lateral side members.

2. The pectus bar extraction tool of claim 1, wherein the protrusion is a hook.

3. The pectus bar extraction tool of claim 2, wherein the width of the hook is less than one-half of the width of the pectus bar.

4. The pectus bar extraction tool of claim 2, wherein the hook extends distally to the handle.

5. The pectus bar extraction tool of claim 1, wherein the lateral side members are rails.

6. The pectus bar extraction tool of claim 1, wherein the handle comprises an indented portion.

7. A method for extracting a pectus bar from a patient, comprising the steps of:

providing a pectus bar having an elongated main body portion with posterior and anterior sides and opposing ends, and engagement structure at said ends for engaging a pectus bar extraction tool, the pectus bar having been surgically implanted in the patient;

providing a pectus bar extraction tool comprising a handle and an engagement member fixed to the handle for cooperating with the engagement structure on the pectus bar;

engaging the engagement member on the pectus bar extraction tool to the engagement structure on one of the opposing ends of the pectus bar;

engaging a second pectus bar extraction tool to the engagement structure at the other opposing end of the pectus bar;

using the handles to apply a straightening force to the pectus bar so as to at least partially straighten the pectus bar, whereby the pectus bar can be removed from the patient.

* * * * *